(12) United States Patent
Allmendinger et al.

(10) Patent No.: US 10,706,537 B2
(45) Date of Patent: Jul. 7, 2020

(54) METHOD FOR CHECKING A MEDICAL IMAGE AND METHOD FOR ADAPTING AN EXAMINATION PROTOCOL DURING A MEDICAL IMAGING EXAMINATION

(71) Applicant: Siemens Healthcare GmbH, Erlangen (DE)

(72) Inventors: Thomas Allmendinger, Forchheim (DE); Matthias Baer, Erlangen (DE); Ute Feuerlein, Erlangen (DE); Christiane Koch, Eggolsheim (DE); Stefan Kaepplinger, Jena (DE); Robert Lapp, Nuremberg (DE); Christian Tietjen, Fuerth (DE); Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 96 days.

(21) Appl. No.: 15/905,919

(22) Filed: Feb. 27, 2018

(65) Prior Publication Data
US 2018/0253842 A1    Sep. 6, 2018

(30) Foreign Application Priority Data
Mar. 1, 2017 (DE) .......................... 10 2017 203 333

(51) Int. Cl.
*G06K 9/00* (2006.01)
*G06T 7/00* (2017.01)
(Continued)

(52) U.S. Cl.
CPC .......... *G06T 7/0012* (2013.01); *G06N 20/00* (2019.01); *G06T 7/0002* (2013.01); *G16H 30/20* (2018.01); *G16H 30/40* (2018.01); *G16H 40/63* (2018.01); *G16H 50/20* (2018.01); *G16H 50/70* (2018.01); *G06K 9/6227* (2013.01); *G06T 2207/10072* (2013.01); *G06T 2207/10081* (2013.01); *G06T 2207/10116* (2013.01); *G06T 2207/20076* (2013.01); *G06T 2207/20081* (2013.01);
(Continued)

(58) Field of Classification Search
CPC ........................................... G06T 2207/20084
See application file for complete search history.

(56) References Cited

U.S. PATENT DOCUMENTS

| 2008/0044069 A1* | 2/2008 | DuGal | G06F 19/321 382/128 |
| 2017/0186157 A1* | 6/2017 | Boettger | A61B 5/748 |

(Continued)

FOREIGN PATENT DOCUMENTS

DE        102014107445 A1    12/2015

OTHER PUBLICATIONS

German Office Action No. 102017203333.9 dated Nov. 16, 2017.

*Primary Examiner* — Oneal R Mistry
(74) *Attorney, Agent, or Firm* — Harness, Dickey & Pierce, P.L.C.

(57) ABSTRACT

A method is for checking a medical image with regard to a processing of the medical image via an image processing module. The method includes providing at least one input requirement of the image processing module relating to at least one image parameter of the medical image; providing the at least one image parameter of the medical image; and checking whether the at least one image parameter fulfills the at least one input requirement.

10 Claims, 8 Drawing Sheets

(51) Int. Cl.
  *G06N 20/00* (2019.01)
  *G16H 50/20* (2018.01)
  *G16H 30/20* (2018.01)
  *G16H 40/63* (2018.01)
  *G16H 50/70* (2018.01)
  *G16H 30/40* (2018.01)
  *G06K 9/62* (2006.01)

(52) U.S. Cl.
  CPC ............... *G06T 2207/20084* (2013.01); *G06T 2207/30004* (2013.01); *G06T 2207/30168* (2013.01)

(56) References Cited

U.S. PATENT DOCUMENTS

2018/0137244 A1* 5/2018 Sorenson ............... G16H 50/20
2018/0144465 A1* 5/2018 Hsieh ........................ G06N 3/08
2018/0235563 A1* 8/2018 Nam ...................... A61B 5/742

\* cited by examiner

METHOD FOR CHECKING A MEDICAL IMAGE AND METHOD FOR ADAPTING AN EXAMINATION PROTOCOL DURING A MEDICAL IMAGING EXAMINATION

PRIORITY STATEMENT

The present application hereby claims priority under 35 U.S.C. § 119 to German patent application number DE 102017203333.9, filed Mar. 1, 2017, the entire contents of which are hereby incorporated herein by reference.

FIELD

At least one embodiment of the invention generally relates to a method for checking a medical image with regard to a processing of the medical image via an image processing module and generally to a method for adapting an examination protocol during a medical imaging examination.

At least one embodiment of the invention further generally relates to a method for generating a list of examination steps as well as to a method for training a decision support system for an examination via a medical imaging device.

At least one embodiment of the invention further generally relates to a data processing unit, a computer program, a computer-readable medium, a decision support system, a medical imaging device, and/or a use of a decision support system.

BACKGROUND

Reproducibility plays a substantial role in quantitative diagnostic findings based on radiological data, in particular image data. Quantitative findings may relate for example to a tumor volume, a tissue density, a calcium score or similar. Comparing the same with corresponding values of a preliminary examination is an everyday task in radiology. Post-processing applications, which are able to derive quantitative information of the aforethe kind from the initially reconstructed image data, generally respond sensitively to changes to relevant image properties, for example to the spatial and/or temporal resolution, the contrasts or similar. Depending on the post-processing application, the data that is to be used as a source for the quantitative evaluation must generally satisfy certain requirements so that the results will be relevant and suitable with regard to reproducibility.

Typically, the use of the right combination of image data and post-processing application for deriving quantitative results is based on knowledge that is described in the documentation, for example in relation to the post-processing application. It is typically left to the user whether data that does not satisfy the requirements with regard to relevance and/or reproducibility is used in a specific post-processing application.

SUMMARY

At least one embodiment of the invention enables a medical imaging examination to be performed in an improved manner.

Advantageous embodiments of the invention are taken into consideration in the claims.

At least one embodiment of the invention relates to a method for checking a medical image with regard to a processing of the medical image via an image processing module, the method comprising:

providing at least one input requirement of the image processing module relating to at least one image parameter of the medical image, providing the at least one image parameter of the medical image, and checking whether the at least one image parameter fulfills the at least one input requirement.

At least one embodiment of the invention further relates to a method for adapting an examination protocol during a medical imaging examination, wherein a list of examination steps is provided, wherein each examination step of the list of examination steps is assigned a respective instruction, wherein the examination protocol comprises a start examination step from the list of examination steps, which start examination step is performed at the commencement of the medical imaging examination, wherein after each performed examination step, the examination protocol is adapted by way of the instruction assigned to the performed examination step by performing one of the following steps based on the instruction:

terminating the medical imaging examination irrespective of a result of the performed examination step, terminating the medical imaging examination as a function of the result of the performed examination step, performing a further examination step from the list of examination steps, which further examination step is specified in the instruction, irrespective of the result of the performed examination step, performing one of a plurality of further examination steps from the list of examination steps, which further examination steps are specified in the instruction, as a function of the result of the performed examination step.

At least one embodiment of the invention further relates to a method for generating a list of examination steps, wherein each examination step is assigned a respective instruction for adapting an examination protocol during a medical imaging examination, the method comprising:

providing a set of training datasets, wherein each training dataset comprises a respective training instruction and an examination parameter set, wherein the examination parameter set relates to an examination step assigned to the training instruction and/or an examination result assigned to the training instruction, and generating the list of examination steps based on the set of training datasets and a machine learning algorithm, wherein each examination step of the list of examination steps is assigned a respective instruction for adapting an examination protocol during a medical imaging examination.

At least one embodiment of the invention further relates to a method for training a decision support system for an examination via a medical imaging device, the method comprising:

providing a set of training datasets, wherein each training dataset comprises a respective training examination job and examination information, wherein the examination information relates to a medical imaging examination that has been performed based on the training examination job, and training the decision support system based on the set of training datasets and a machine learning algorithm in such a way that via the trained decision support system it is possible to generate an examination recommendation for the examination via the medical imaging device based on an examination job.

At least one embodiment of the invention further relates to a data processing unit which is embodied to perform a method according to one of the embodiments disclosed in this application.

At least one embodiment of the invention further relates to a computer program which can be loaded into a memory device of a data processing system and has program sections for performing all steps of a method according to one of the embodiments disclosed in this application when the computer program is executed by the data processing system.

At least one embodiment of the invention further relates to a computer-readable medium on which are stored program sections that can be read in and executed by a data processing system in order to perform all steps of a method according to one of the embodiments disclosed in this application when the program sections are executed by the data processing system.

At least one embodiment of the invention further relates to a decision support system which has been trained based on a method according to one of the embodiments disclosed in this application.

At least one embodiment of the invention further relates to a medical imaging device comprising a data processing unit according to one of the embodiments disclosed in this application and/or a decision support system according to one of the embodiments disclosed in this application.

At least one embodiment of the invention further relates to a use of a decision support system which has been trained based on a method according to one of the embodiments disclosed in this application in a medical imaging device and/or for generating an examination recommendation for an examination via a medical imaging device based on an examination job.

BRIEF DESCRIPTION OF THE DRAWINGS

Selected embodiment variants of the invention are explained below with reference to the attached figures. The illustration in the figures is schematic, greatly simplified and not necessarily true to scale.

In the figures.

DETAILED DESCRIPTION OF THE EXAMPLE EMBODIMENTS

Figure 1:
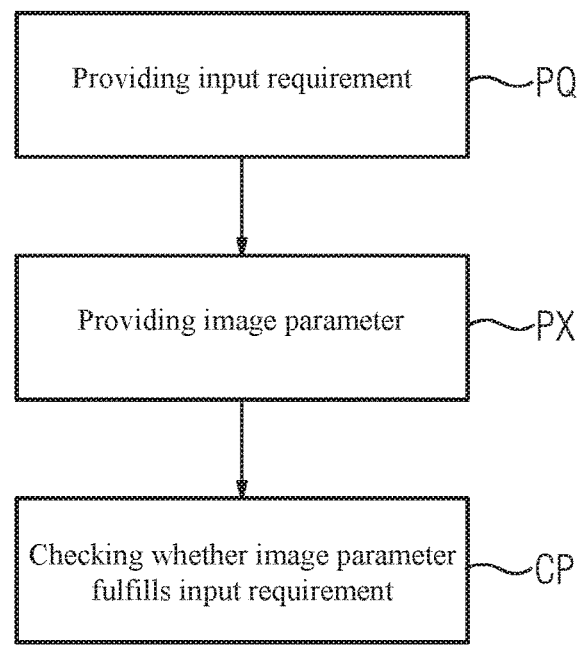
FIG. 1 shows a flowchart for a method for checking a medical image with regard to a processing of the medical image via an image processing module according to an embodiment variant of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for checking a medical image with regard to a processing of the medical image via an image processing module, the method comprising:

providing at least one input requirement of the image processing module relating to at least one image parameter of the medical image, providing the at least one image parameter of the medical image, and checking whether the at least one image parameter fulfills the at least one input requirement.

In particular, the medical image may be a medical computed tomography image. In particular, the medical imaging examination may be a medical computed tomography imaging examination.

In particular, the following step may be performed as a function of a result of the check:

outputting an alert relating to a quality of an image processing result of the processing of the medical image via the image processing module.

In particular, one of the following steps may be performed as a function of a result of the check:

processing the medical image via the image processing module, rejecting an image processing job relating to the processing of the medical image via the image processing module.

In particular, the following step may be performed as a function of a result of the check:

generating an image generation job for a further medical image based on the at least one input requirement.

In particular, the method may additionally comprise the following steps:

generating a further medical image based on the image generation job for the further medical image, providing at least one image parameter of the further medical image, checking whether the at least one image parameter of the further medical image fulfills the at least one input requirement.

In particular, the method may additionally comprise the following steps:

generating an image generation job for the medical image based on the at least one input requirement, generating the medical image based on the image generation job for the medical image.

In particular, the at least one input requirement may be defined independently of specific characteristics of a medical imaging device by which the medical image and/or the further medical image are/is generated.

In particular, the at least one image parameter may be chosen from the image parameter group consisting of a spatial resolution, a temporal resolution, an edge behavior, a contrast, a convolution kernel, a slice thickness, a rotation time, a pitch, a tube voltage, a filter property, a modulation transfer function, and combinations thereof.

At least one embodiment of the invention further relates to a method for adapting an examination protocol during a medical imaging examination, wherein a list of examination steps is provided, wherein each examination step of the list of examination steps is assigned a respective instruction, wherein the examination protocol comprises a start examination step from the list of examination steps, which start examination step is performed at the commencement of the medical imaging examination, wherein after each performed examination step, the examination protocol is adapted by way of the instruction assigned to the performed examination step by performing one of the following steps based on the instruction:

terminating the medical imaging examination irrespective of a result of the performed examination step, terminating the medical imaging examination as a function of the result of the performed examination step, performing a further examination step from the list of examination steps, which further examination step is specified in the instruction, irrespective of the result of the performed examination step, and performing one of a plurality of further examination steps from the list of examination steps, which further examination steps are specified in the instruction, as a function of the result of the performed examination step.

In particular, the following step may be performed as a function of a result of the performed examination step:

generating an image generation job for a further medical imaging examination based on the instruction and/or the result of the performed examination step.

In particular, the method may additionally comprise the following step:

determining the result of the performed examination step based on a user input and/or based on an automatic evaluation of data that was acquired during the performed examination step.

At least one embodiment of the invention further relates to a method for generating a list of examination steps, wherein each examination step is assigned a respective instruction for adapting an examination protocol during a medical imaging examination, the method comprising:

providing a set of training datasets, wherein each training dataset comprises a respective training instruction and an examination parameter set, wherein the examination parameter set relates to an examination step assigned to the training instruction and/or an examination result assigned to the training instruction, and generating the list of examination steps based on the set of training datasets and a machine learning algorithm, wherein each examination step of the list of examination steps is assigned a respective instruction for adapting an examination protocol during a medical imaging examination.

In particular, at least one training dataset of the set of training datasets may be provided by performing the following steps during the course of an examination:

recording a deviation from a selected examination protocol, which deviation was initiated manually by a user following a performed examination step, as a training instruction, recording an examination parameter set relating to the performed examination step and/or to an examination result of the performed examination step.

At least one embodiment of the invention further relates to a method for training a decision support system for an examination via a medical imaging device, the method comprising:

providing a set of training datasets, wherein each training dataset comprises a respective training examination job and examination information, wherein the examination information relates to a medical imaging examination that has been performed based on the training examination job, and training the decision support system based on the set of training datasets and a machine learning algorithm in such a way that via the trained decision support system it is possible to generate an examination recommendation for the examination via the medical imaging device based on an examination job.

According to an embodiment variant of the invention it is provided that the training examination job comprises a training instruction, that the examination information comprises an examination parameter set, wherein the examination parameter set relates to an examination step that is assigned to the training instruction and/or to an examination result that is assigned to the training instruction, that the examination recommendation comprises a list of examination steps that is generated based on the set of training datasets and the machine learning algorithm, wherein each examination step of the list of examination steps is assigned a respective instruction for adapting an examination protocol during a medical imaging examination.

According to an embodiment variant of the invention it is provided that the training examination job comprises an image generation job, that the examination information comprises acquisition parameters and/or reconstruction parameters by which the image generation job was performed during the medical imaging examination.

According to an embodiment variant of the invention it is provided that the training examination job comprises an image processing job, that the examination information comprises image processing parameters by which the image processing job was performed during the medical imaging examination.

At least one embodiment of the invention further relates to a data processing unit which is embodied to perform a method according to one of the embodiments disclosed in this application.

At least one embodiment of the invention further relates to a computer program which can be loaded into a memory device of a data processing system and has program sections for performing all steps of a method according to one of the embodiments disclosed in this application when the computer program is executed by the data processing system.

At least one embodiment of the invention further relates to a computer-readable medium on which are stored program sections that can be read in and executed by a data processing system in order to perform all steps of a method according to one of the embodiments disclosed in this application when the program sections are executed by the data processing system.

At least one embodiment of the invention further relates to a decision support system which has been trained based on a method according to one of the embodiments disclosed in this application.

At least one embodiment of the invention further relates to a medical imaging device comprising a data processing unit according to one of the embodiments disclosed in this application and/or a decision support system according to one of the embodiments disclosed in this application.

At least one embodiment of the invention further relates to a use of a decision support system which has been trained based on a method according to one of the embodiments disclosed in this application in a medical imaging device and/or for generating an examination recommendation for an examination via a medical imaging device based on an examination job.

Given knowledge of the mode of operation of a post-processing algorithm, it is possible to specify necessary and/or sufficient properties of input data, in particular of the medical image, which characterize a suitability of the input data for an evaluation by way of the post-processing algorithm. With a trained post-processing algorithm, the properties can be specified, in particular with knowledge of the properties of the training data and under the assumption that the result aimed at by way of the trained algorithm functions in an optimal manner with the training data. In the context of the present application, the terms post-processing module and image processing module are used synonymously.

The properties may relate for example to a spatial resolution in one or more spatial directions, an edge behavior, in particular an overshoot, a temporal resolution, in particular a minimum temporal resolution, a material contrast or similar.

The properties may correlate in particular with acquisition parameters and/or reconstruction parameters. Examples of acquisition parameters and/or reconstruction parameters are in particular a convolution kernel, a slice thickness, a rotation time, a pitch, a reconstructed data segment, a tube voltage or a filtering property. In particular, the spatial resolution correlates with the convolution kernel and/or with the slice thickness, the edge behavior with the convolution kernel, the temporal resolution with the rotation time, with the pitch and/or with the reconstructed data segment, the material contrast with the tube voltage and/or with the filtering property.

In particular, a selection of the aforementioned parameters may be used to characterize the medical image. Moreover, further parameters may be added without leaving the scope of the invention insofar as it is set out by the claims. In addition to fixed values in each case, intervals or a list of values may also be defined in particular for the at least one image parameter by way of the at least one input requirement. The medical image may in particular comprise a header and/or a footer.

The image processing module may in particular be an image processing algorithm and/or include an image processing algorithm. The image processing module may for example be embodied for segmenting a structure and/or for extracting a centerline in the medical image. The image processing module may in particular be integrated into a post-processing application. The post-processing application may for example be embodied for detecting pulmonary nodules and/or for detecting a stenosis.

Preferably, the input requirements are stored in a standardized form, in particular irrespective of specialized imaging devices and/or manufacturers.

For example, modulation transfer functions may be specified for one or more or all spatial directions instead of the convolution kernel and the slice thickness. The modulation transfer functions can be realized in particular when a specific convolution kernel is used and a specific slice thickness is set. In this way it is possible for example to describe the spatial resolution and the edge behavior in a device-neutral manner.

The medical imaging device may for example be chosen from the imaging modalities group consisting of an x-ray device, a C-arm x-ray device, a computed tomography device (CT device), a molecular imaging device (MI device), a single-photon emission computed tomography device (SPECT device), a positron emission tomography device (PET device), a magnetic resonance tomography device (MR device), and combinations thereof, in particular a PET/CT device and a PET/MR device. The medical imaging device may furthermore comprise a combination of an imaging modality, chosen for example from the imaging modalities group, and an irradiation modality. In this case the irradiation modality may for example comprise an irradiation unit for therapeutic irradiation treatment.

Without limiting the general inventive concept, a computed tomography device is cited in relation to some of the embodiment variants by way of example for a medical imaging device.

According to an embodiment variant of the invention, the medical imaging device comprises an acquisition unit which is embodied for acquiring the acquisition data. In particular, the acquisition unit may comprise a radiation source and a radiation detector.

An embodiment variant of the invention provides that the radiation source is embodied for emitting and/or exciting radiation, in particular electromagnetic radiation, and/or that the radiation detector is embodied for detecting the radiation, in particular the electromagnetic radiation. The radiation may for example travel from the radiation source to a region to be imaged and/or arrive at the radiation detector following an interaction with the region to be imaged.

During the interaction with the region to be imaged, the radiation is modified and thus becomes a carrier of information relating to the region to be imaged. During the interaction of the radiation with the detector, the information is captured in the form of acquisition data.

In particular in the case of a computed tomography device and in the case of a C-arm x-ray device, the acquisition data may be projection data, the acquisition unit a projection data acquisition unit, the radiation source an x-ray source, and the radiation detector an x-ray detector. The x-ray detector may in particular be a quantum-counting and/or energy-resolving x-ray detector.

In particular in the case of a magnetic resonance tomography device, the acquisition data may be a magnetic resonance dataset, the acquisition unit a magnetic resonance data acquisition unit, the radiation source a first radiofrequency antenna unit, and the radiation detector the first radiofrequency antenna unit and/or a second radiofrequency antenna unit.

The data processing unit and/or one or more components of the data processing unit may be formed by a data processing system. The decision support system and/or one or more components of the decision support system may be formed by a data processing system.

The data processing system may for example comprise one or more components in the form of hardware and/or one or more components in the form of software.

The data processing system may for example be formed at least in part by a cloud computing system.

The data processing system may for example be and/or comprise a cloud computing system, a computer network, a computer, a tablet computer, a smartphone or similar, or combinations thereof. The hardware may for example cooperate with software and/or be configurable via software. The software may for example be executed via the hardware.

The hardware may for example be a storage system, an FPGA (Field-Programmable Gate Array) system, an ASIC (Application-Specific Integrated Circuit) system, a microcontroller system, a processor system, and combinations thereof. The processor system may for example comprise a microprocessor and/or a plurality of cooperating microprocessors.

In particular, a component of the data processing unit according to one of the aspects disclosed in this application, which component is embodied to perform a given step of a method according to one of the embodiments disclosed in this application, may be implemented in the form of hardware which is configured to perform the given step and/or which is configured to execute a computer-readable instruction in such a way that the hardware may be configured via the computer-readable instruction to perform the given step. In particular, the system may comprise a storage area, for example in the form of a computer-readable medium, in which computer-readable instructions, for example in the form of a computer program, are stored.

A data transfer between components of the data processing system may for example be performed in each case via a suitable data transfer interface. The data transfer interface for transferring data to and/or from a component of the data processing system may be realized at least in part in the form of software and/or at least in part in the form of hardware. The data transfer interface may for example be embodied for storing data in and/or for loading data from an area of the storage system, one or more components of the data processing system being able to access the area of the storage system.

The computer program is loadable into the storage system of the data processing system and can be executed by the processor system of the data processing system.

The data processing system may for example be embodied via the computer program in such a way that the data processing system can perform the steps of a method according to one of the embodiment variants disclosed in this application when the computer program is executed by the data processing system.

The computer program product according to one of the embodiment variants disclosed in this application and/or the computer program according to one of the embodiment variants disclosed in this application may for example be stored on the computer-readable medium.

The computer-readable medium may for example be a memory stick, a hard disk or another data medium which in particular may be releasably connected to the data processing system or permanently integrated into the data processing system. The computer-readable medium may for example form a domain of the storage system of the data processing system. In the context of the present application, the terms protocol and examination protocol are used synonymously for one another.

Within the scope of the invention, features which are described in relation to different embodiment variants of the invention and/or different claims categories (method, use, device, system, arrangement, etc.) may be combined to form further embodiment variants of the invention. For example, a claim relating to a device may also be developed using features that are described or claimed in connection with a method. At the same time, functional features of a method may be implemented via correspondingly embodied material components. In addition to the embodiment variants of the invention explicitly described in this application, myriad further embodiment variants of the invention which the person skilled in the art may arrive at are conceivable without leaving the scope of the invention insofar as it is set out by the claims.

The use of the indefinite articles "a" or "an" does not exclude the possibility that the feature in question may also be present more than once. The use of the term "comprise" does not rule out the possibility that the concepts linked by way of the term "comprise" may be identical. For example, the medical imaging device comprises the medical imaging device. The use of the term "unit" does not rule out the possibility that the object to which the term "unit" refers may comprise a plurality of components that are separated from one another in space.

The phrase "based on" may be understood in the context of the present application in particular in the sense of the term "using". In particular, a formulation which accordingly produces (alternatively: determines, defines, etc.) a first feature based on a second feature does not preclude the possibility that the first feature may be produced (alternatively: determined, defined, etc.) based on a third feature.

FIG. 1 shows a flowchart for a method for checking a medical image with regard to a processing of the medical image via an image processing module according to an embodiment variant of the invention, wherein the method comprises the following steps:

providing PQ at least one input requirement of the image processing module relating to at least one image parameter of the medical image, providing PX the at least one image parameter of the medical image, checking CP whether the at least one image parameter fulfills the at least one input requirement.

Figure 2:
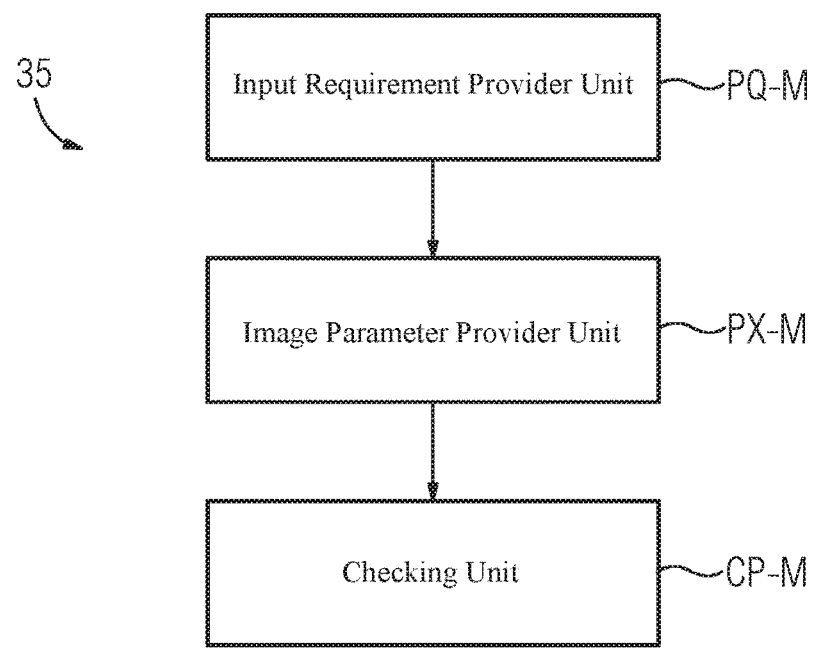
FIG. 2 shows a schematic representation of a data processing unit for checking a medical image with regard to a processing of the medical image via an image processing module according to a further embodiment variant of the invention.

FIG. 2 shows a schematic representation of a data processing unit 35 for checking a medical image with regard to a processing of the medical image via an image processing module according to a further embodiment variant of the invention, comprising:

an input requirement provider unit PQ-M for providing PQ at least one input requirement of the image processing module relating to at least one image parameter of the medical image, an image parameter provider unit PX-M for providing PM the at least one image parameter of the medical image, a checking unit CP-M for checking CP whether the at least one image parameter fulfills the at least one input requirement.

Figure 3:
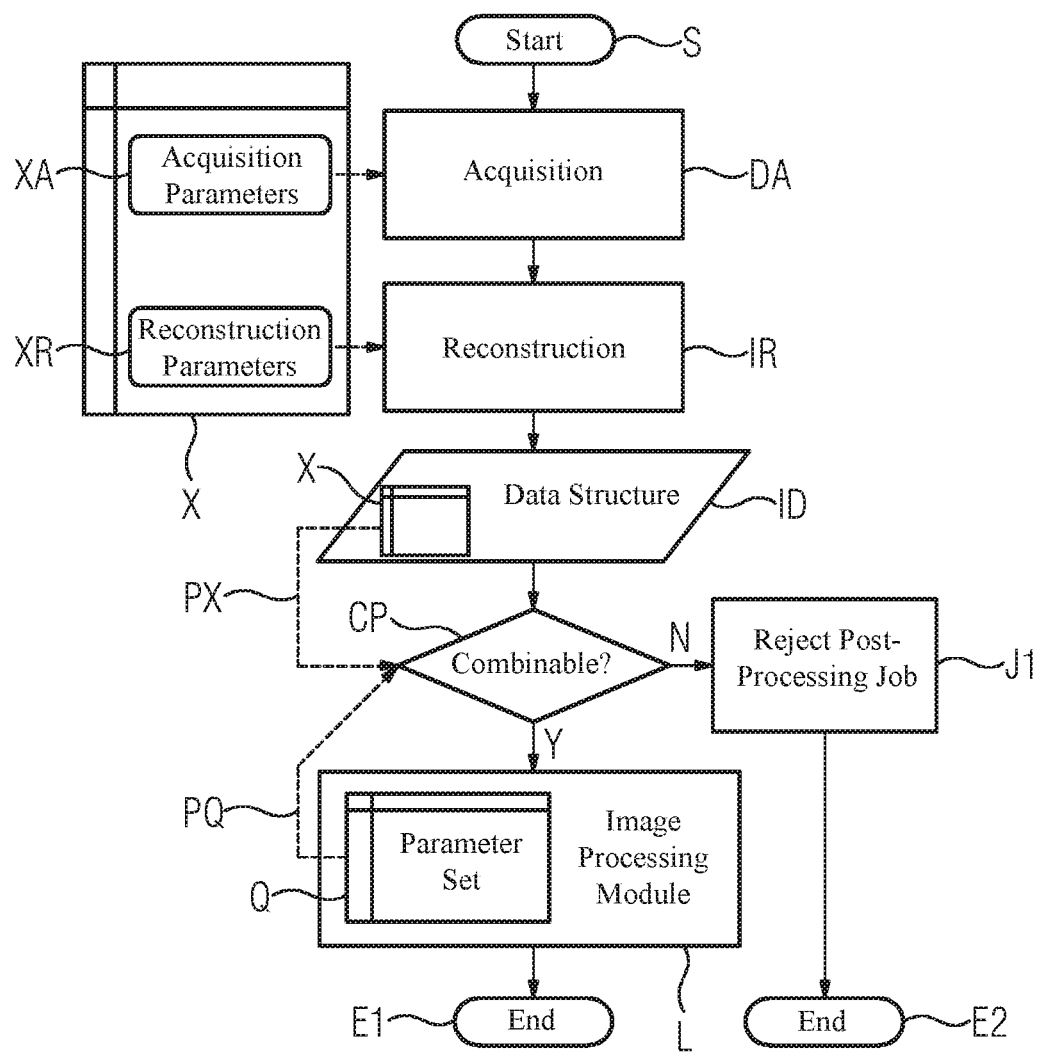
FIG. 3 shows a flowchart for a method for checking a medical image with regard to a processing of the medical image via an image processing module according to a further embodiment variant of the invention.

FIG. 3 shows a flowchart for a method for checking a medical image with regard to a processing of the medical image via an image processing module according to an embodiment variant of the invention. The start of the execution sequence of the method is marked by step S.

In this case, a parameter set $P_{algo}$ is assigned to a post-processing module L which describes the input requirements and/or is stored in the post-processing module.

Within the meaning of the above parameter model, the image parameters, $P_{real}$, realized in the medical image are stored in a data structure ID in which the medical image is transmitted. A header or footer may be used for this purpose, for example. $P_{algo}$ is represented by reference sign Q. $P_{real}$ is represented by reference sign X. $P_{real}$ may comprise acquisition parameters XA for an acquisition DA and/or reconstruction parameters XR for a reconstruction IR.

Next, at step CP, a check is carried out to verify whether $P_{real}$ may be combined with $P_{algo}$. This can be realized in particular by way of a parameter-by-parameter check to determine whether the realized value lies in the value range specified via $P_{algo}$. The value range may for example be specified in the form of a value, an interval and/or a list. $P_{real}$ and $P_{algo}$ may be regarded in principle as sets of values for specific parameters. The check to verify whether the at least one image parameter fulfills the at least one input requirement would therefore correspond to the check to determine whether $P_{real}$ is a subset of $P_{algo}$, i.e. whether $P_{real} \subseteq P_{algo}$ applies.

Figure 4:
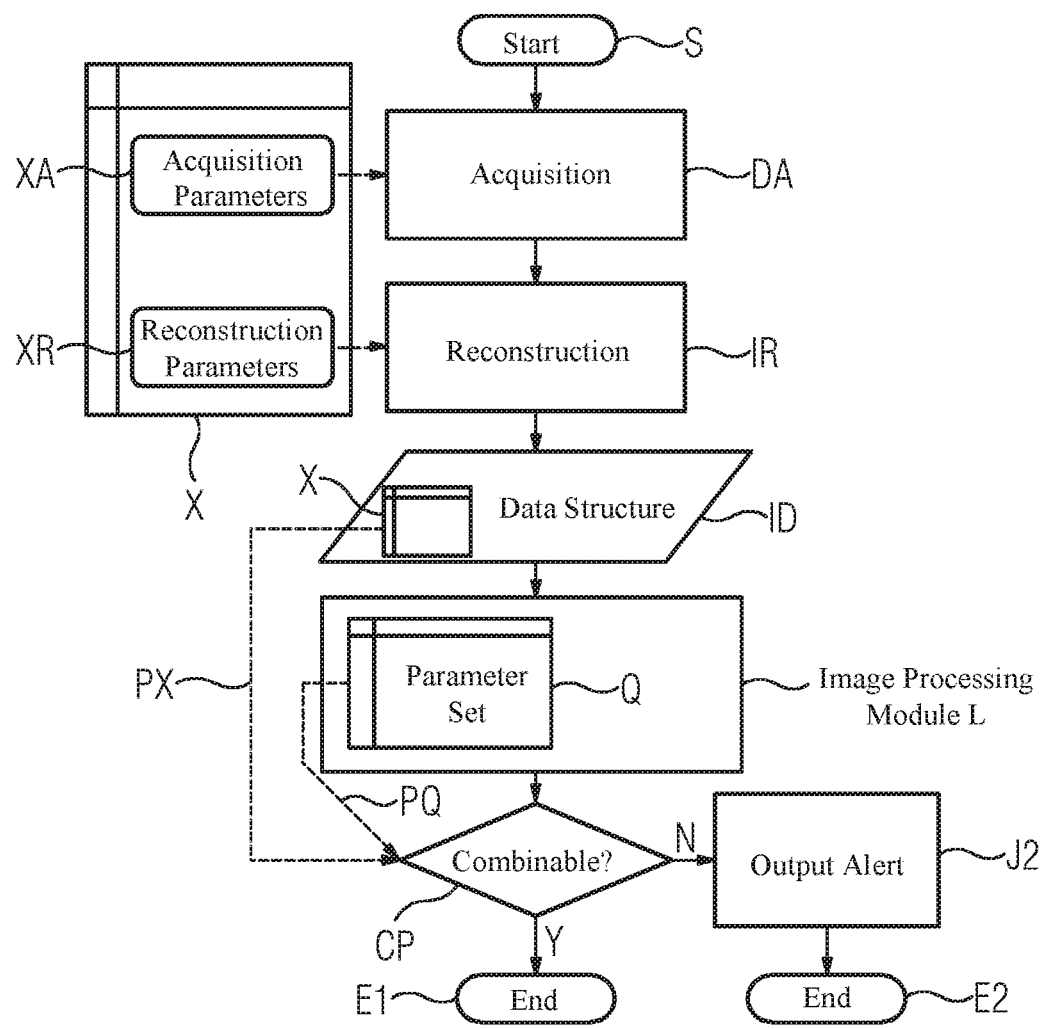
FIG. 4 shows a flowchart for a method for checking a medical image with regard to a processing of the medical image via an image processing module according to a further embodiment variant of the invention.

If this requirement is fulfilled, the medical image is processed via the image processing module L. This path is marked by Y. Otherwise, as shown in FIG. 3, the post-processing job is rejected J1 and/or, as shown in FIG. 4, an alert J2 is output to the user indicating that the results generated via the post-processing algorithm may possibly be limited in terms of their quality. This path is marked by N. An end of the execution sequence of the method is marked by steps E1 and E2, respectively.

Figure 5:
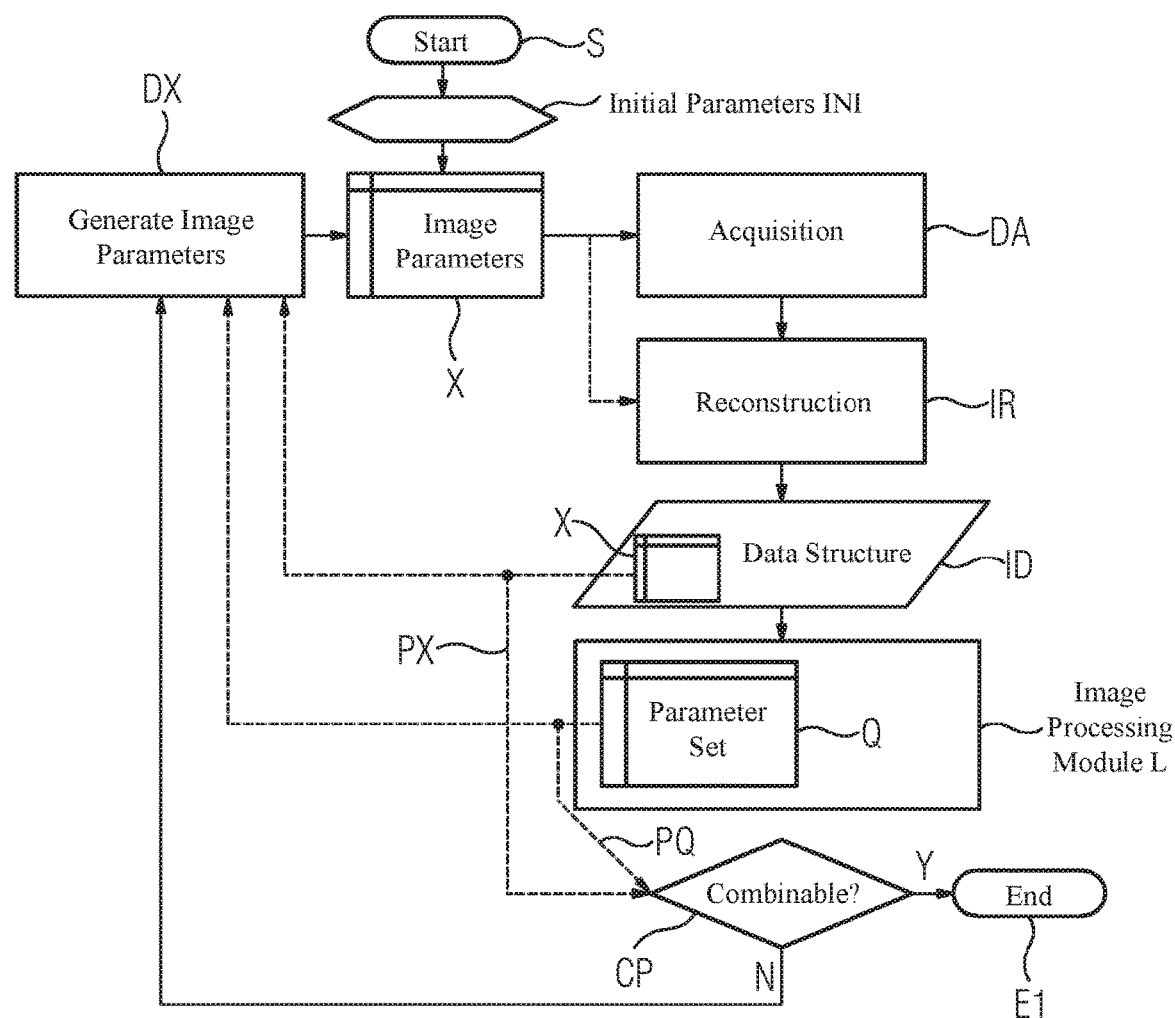
FIG. 5 shows a flowchart for a method for checking a medical image with regard to a processing of the medical image via an image processing module according to a further embodiment variant of the invention.

In the embodiment variant of the invention shown in FIG. 5, if the at least one image parameter does not fulfill the at least one input requirement, an image generation job is generated relating to a generation of a further medical image taking into consideration the at least one input requirement $P_{algo}$. Based on the image generation job, a further medical image which fulfills the requirement $P_{real} \subseteq P_{algo}$ can be generated via a medical imaging device.

At step DX, image parameters, in particular acquisition parameters and/or reconstruction parameters for generating the further medical image, are generated based on $P_{real}$ and/or $P_{algo}$ and/or on a result of the check CP. These parameters are different in particular from the initial parameters that were provided for generating the medical image at step INI. The generation of the further medical image may in particular comprise a reconstruction of the further medical image based on already acquired raw data. For example, the same raw data may be used in this case as was used already for a reconstruction of the medical image that does not fulfill the at least one input requirement. In this case use may be made in particular of reconstruction parameters that are adapted to the at least one input requirement.

The generation of the further medical image may include an acquisition of raw data via a medical imaging device, in particular when the requirement $P_{real} \subseteq P_{algo}$ cannot be fulfilled by way of the reconstruction alone. In particular, acquisition parameters may be used in this case which are adapted to the at least one input requirement. The further medical image may be reconstructed based on the thus acquired raw data.

The solution according to an embodiment of the invention therefore enables an automatic control of an acquisition and/or a reconstruction which is adapted with regard to a processing of a medical image generated in the process via a post-processing application. Including a new acquisition of data makes sense in particular for modalities in which this does not cause the patient to be subjected to any additional exposure, for example due to ionizing radiation.

If it is not possible to fulfill the condition $P_{real} \subseteq P_{algo}$ based on the further medical image, the post-processing job can be rejected and/or an alert can be output to the user indicating that the results generated via the post-processing algorithm could be limited in terms of their quality.

Figure 6:
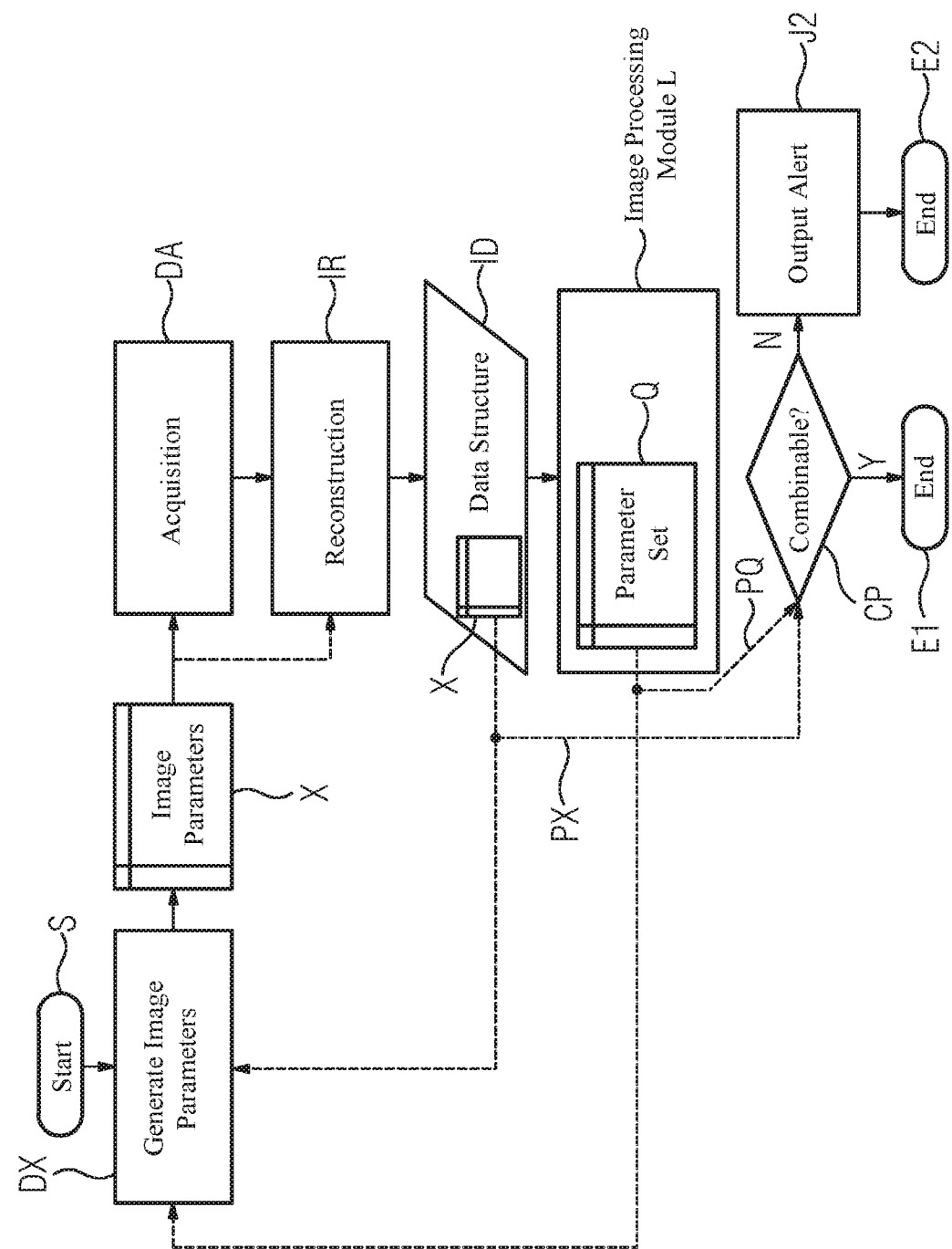
FIG. 6 shows a flowchart for a method for checking a medical image with regard to a processing of the medical image via an image processing module according to a further embodiment variant of the invention.

In the embodiment variant shown in FIG. 6, the medical image on which the first checking step is based is already generated based on an image generation job which was generated based on the at least one input requirement.

In particular, an image generation job may be generated based on a planned post-processing step with specification of the input requirements $P_{algo}$ for generating a medical image and output to a medical imaging device.

In particular, a medical image may be generated based on the image generation job via a medical imaging device in such a way that the at least one image parameter of the further medical image fulfills the at least one input requirement. The generation of the medical image may in particular include a reconstruction and/or an acquisition.

In particular, a reconstruction of already acquired raw data may be carried out based on the image generation job for the medical image using reconstruction parameters that are adapted to the at least one input requirement. This is aimed at fulfilling or at least approximately fulfilling the requirement $P_{real} \subseteq P_{algo}$ for the medical image. In particular when the requirement $P_{real} \subseteq P_{algo}$ for the medical image cannot be fulfilled by way of the reconstruction alone, an acquisition can be performed based on the image generation job for the medical image using acquisition parameters that are adapted to the at least one input requirement. The thus acquired raw data may be reconstructed in particular using reconstruction parameters that are adapted to the at least one input requirement.

For example, a check based on a reconstruction using reconstruction parameters that are adapted to the at least one input requirement may be carried out initially in order to determine whether the at least one input requirement for the medical image is fulfilled. If the at least one input requirement for the medical image is not fulfilled, an image generation job for a further medical image can be generated which relates both to an acquisition and to a reconstruction. If the requirement $P_{real} \subseteq P_{algo}$ is fulfilled, the post-processing step can be performed. Otherwise, the post-processing job is rejected and/or an alert is output to the user indicating that the results generated via the post-processing algorithm may possibly be limited in terms of their quality.

The solution according to an embodiment of the invention enables in particular a check to be carried out in order to determine whether a medical image is actually suitable as a basis for a post-processing operation. In this way it is possible in particular to realize an improvement in quality with regard to the accuracy and/or the reproducibility of the results derived on the basis of the post-processing operation. It is furthermore possible to advise caution be exercised in the interpretation of the results.

The best possible quality in the chain of acquisition, reconstruction and derivation of results via post-processing algorithms can be achieved retrospectively or in advance with the aid of the image generation job. The method steps can be performed in particular in an automated manner. This is associated with a reduction in the amount of effort required, or at least no increase in the amount of effort required, on the part of the user.

In radiological examinations, diagnostic findings may emerge during the procedure which necessitate an individual modification or extension of the examination protocol.

In particular when the examination is intended to rule out a number of grounds for suspicion, the examination protocol is typically configured in such a way that the maximum chain of examination steps that might be necessary in order to rule out a ground for suspicion can be processed.

In this case a linear sequence of examination steps may be used that corresponds to a superset of the necessary examination steps. The examination steps may for example be scans in the case of different physiological states, in particular native scans, scans using contrast agent, scans at different phases or similar.

After each examination step it is decided as a function of the respective findings whether the protocol may be terminated prematurely or a step skipped or a transition made to the next examination step in the sequence. This typically happens manually on the basis of indication-based rules of the respective institution and/or of the general evidence base of the user.

In the event of an incidental finding, a modification of the examination and/or an additional examination may be necessary. Regardless of whether this is carried out immediately afterward or at another appointment, a new examination job must usually be set up manually.

The solution according to an embodiment of the invention in particular enables these dynamic adjustments to be simplified and/or automated.

Each of the subject matters of the independent claims achieves this object in each case. Further advantageous aspects of the invention are taken into consideration in the dependent claims.

In particular, a basic protocol can be defined which contains the list of examination steps. Such a basic protocol may also be understood for example as a superset of a maximum examination scope that can be planned using the examination steps. The examination steps may for example be borrowed from a conventional examination protocol.

The assignment of the instructions to the examination steps may be carried out manually within the scope of an implementation. Alternatively or in addition, the list of examination steps may be machine-learned in conjunction with the instructions from medical imaging examinations in which conventional examination protocols are used. In the process, the user may then for example be asked for the reason if there is a deviation from the linear sequence of examination steps that is provided in the conventional protocol during the medical imaging examination.

Such a deviation may involve in particular a skipping of an examination step in the linear sequence, a premature termination of the medical imaging examination or similar. In particular, the examination parameter set of the training dataset may include the reason for the deviation. According to an embodiment variant of the invention, with the exception of the start examination step, the order of the examination steps in the list of examination steps is of no importance per se. Except for the start examination step, whether the examination step is performed in this case is not dependent on the relative position of an examination step in the list. Rather, what matters is whether a previously performed examination step is assigned an instruction which points to the examination step that is to be performed thereafter.

According to an embodiment variant of the invention, at least one examination step is assigned an instruction which points to the next examination step that is to be performed, without any further condition with regard to the result of the examination step, or which terminates the entire examination. According to an embodiment variant of the invention, at least one examination step is assigned an instruction which points to one of a plurality of examination steps as a function of a result of the examination step relating to the problem that the examination is intended to answer, or which terminates the entire examination sequence.

According to an embodiment variant of the invention, at least one examination step is assigned an instruction which defines a further indication for a subsequent examination as a function of an in particular unexpected finding, and/or which selects a further examination protocol in respect of a clinical problem relating to the finding.

The instruction may in particular comprise a generation of an examination job (Requested Procedure/Modality Worklist) in an HIS/RIS (Hospital Information System/Radiology Information System).

According to an embodiment variant of the invention, the result of the performed examination step is determined based on an interaction with the user, for example a user of a medical imaging device. The interaction may in particular comprise a question that is to be answered by a user and/or a list of options from which the user can select the answer.

According to an embodiment variant of the invention, the result of the performed examination step is determined based on an automatic analysis of data generated in the course of the performed examination step. The data may for example consist of slice images, post-processing results or similar.

In particular, it is possible to adapt an examination protocol for coronary heart disease based on an automatically calculated calcium score during a medical imaging examination.

Figure 7:
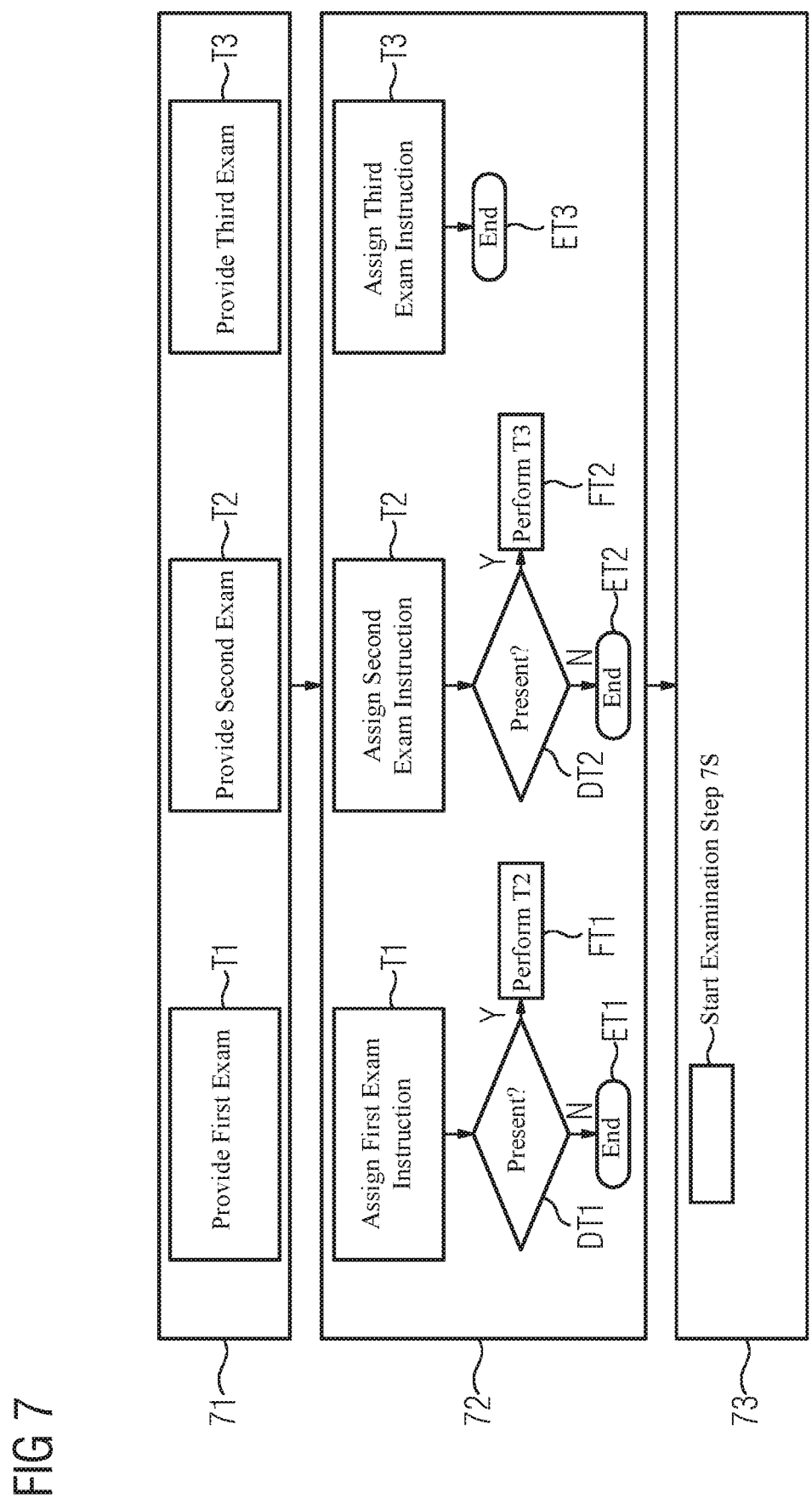
FIG. 7 shows a flowchart for a method for adapting an examination protocol during a medical imaging examination.

FIG. 7 shows a schematic representation of an examination protocol for the exclusion of hemorrhaging, infarction and/or tumor in the brain. A list of examination steps T1, T2, T3 is provided at step 71.

At step 72, each examination step in the list of examination steps is assigned a respective instruction. At step 73, start examination step 7S is defined, specifying, for example, that the examination protocol is to commence with examination step T1.

Examination step T1 may in particular relate to an examination of soft tissue without contrast agent. Examination step T2 may in particular relate to an examination of soft tissue with contrast agent, for example with delayed administration of contrast agent. Examination step T3 may in particular relate to an examination of a tumor volume with contrast agent, for example with delayed administration of contrast agent.

At step DT1, it can be determined in particular whether hemorrhaging or an infarction is present. If yes Y, the examination is continued with examination step T2 according to instruction FT1. If no N, the examination is terminated according to instruction ET1. At step DT2, it can be determined in particular whether a tumor is present. If yes Y, the examination is continued with examination step T3 according to instruction FT2. If no N, the examination is terminated according to instruction ET2.

After examination step T3 has been performed, the examination is terminated according to instruction ET3.

Figure 8:
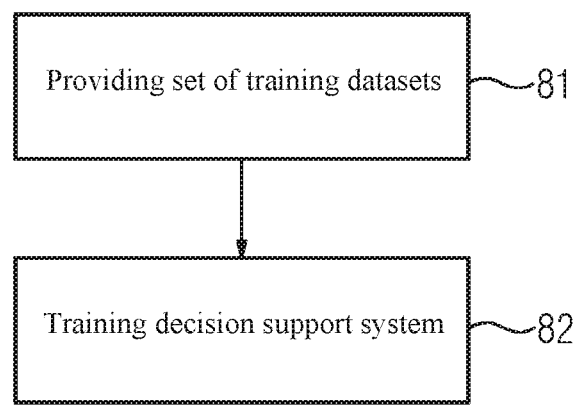
FIG. 8 shows a flowchart for a method for training a decision support system for an examination via a medical imaging device.

FIG. 8 shows a flowchart for a method for training a decision support system for an examination via a medical imaging device, wherein the method comprises the following steps:

providing 81 a set of training datasets, wherein each training dataset comprises a respective training examination job and examination information, wherein the examination information relates to a medical imaging examination that has been carried out based on the training examination job, training 82 the decision support system based on the set of training datasets and a machine learning algorithm in such a way that via the trained decision support system it is possible to generate an in particular optimal examination recommendation for the examination via the medical imaging device based on an examination job.

Figure 9:
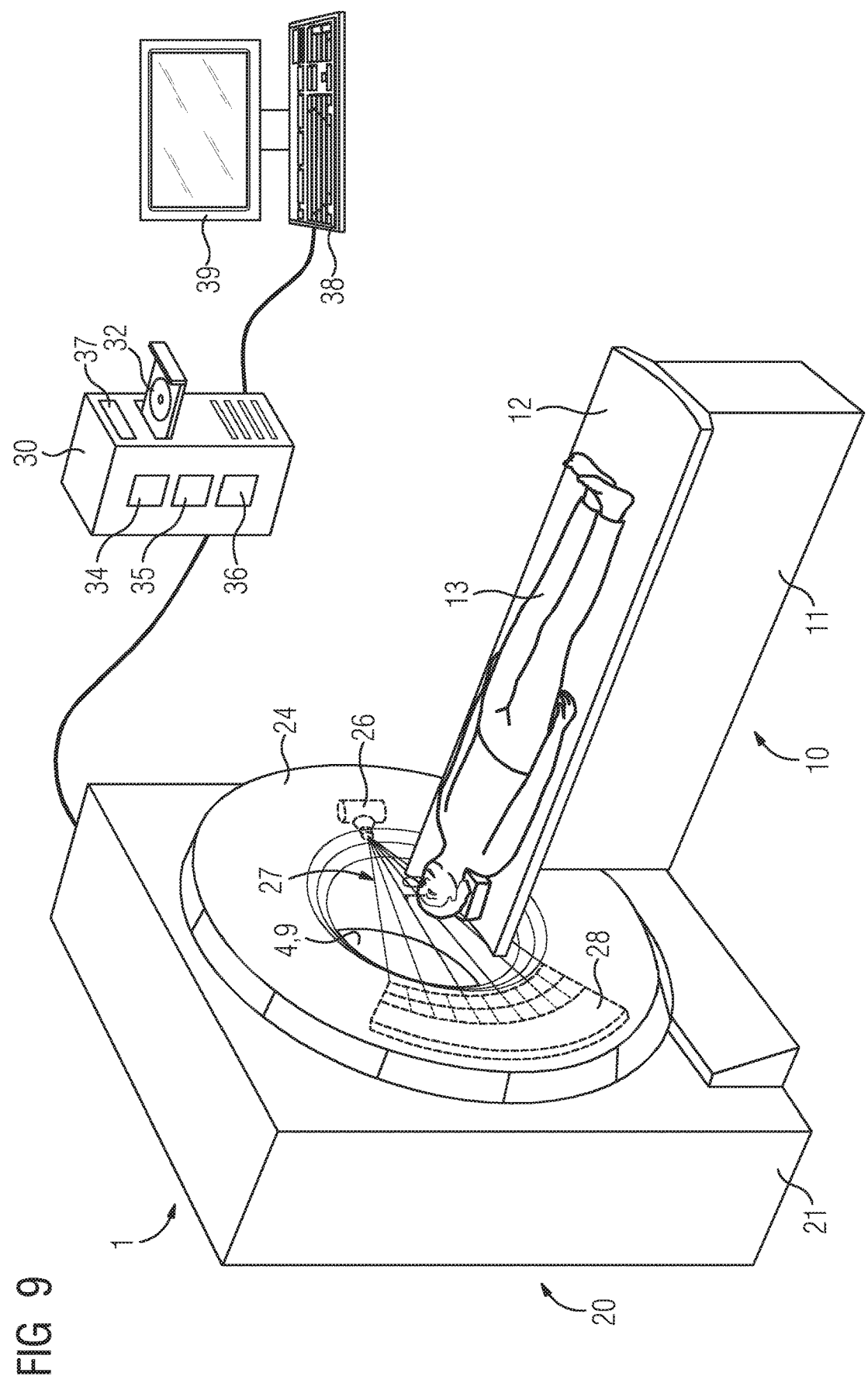
FIG. 9 shows a schematic representation of a medical imaging device according to an embodiment variant of the invention.

FIG. 9 shows a schematic representation of a medical imaging device 1 according to an embodiment variant of the invention. Without limiting the general inventive concept, a computed tomography device is shown by way of example for the medical imaging device 1. The medical imaging device 1 comprises the gantry 20, the tunnel-shaped opening or bore 9, the patient support device 10 and the control device 30. The gantry 20 comprises the stationary carrier frame 21 and the rotor 24.

The patient 13 can be introduced into the tunnel-shaped bore 9. The acquisition zone 4 is located in the tunnel-shaped bore 9. A region to be imaged of the patient 13 can be positioned in the acquisition zone 4 in such a way that the radiation 27 can travel from the radiation source 26 to the region to be imaged and, after interacting with the region to be imaged, can arrive at the radiation detector 28.

The patient support device 10 comprises the support plinth 11 and the support tabletop 12 for supporting the patient 13. The support tabletop 12 is arranged on the support plinth 11 so as to be movable relative to the support plinth 11 in such a way that the support tabletop 12 can be introduced into the acquisition zone 4 in a longitudinal direction of the support tabletop 12, in particular along the system axis AR.

The medical imaging device 1 is embodied for acquiring acquisition data based on electromagnetic radiation 27. The medical imaging device 1 comprises an acquisition unit. The acquisition unit is a projection data acquisition unit comprising the radiation source 26, e.g. an x-ray source, and the detector 28, e.g. an x-ray detector, in particular an energy-resolving x-ray detector.

The radiation source 26 is arranged on the rotor 24 and is embodied for emitting radiation 27, e.g. x-ray radiation, comprising radiation quanta 27. The detector 28 is arranged on the rotor 24 and is embodied for detecting the radiation quanta 27. The radiation quanta 27 can travel from the radiation source 26 to the region to be imaged of the patient 13 and, after interacting with the region to be imaged, impinge on the detector 28. In this way, acquisition data of the region to be imaged can be captured in the form of projection data via the acquisition unit.

The control device 30 is embodied for receiving the acquisition data acquired by the acquisition unit. The control device 30 is embodied for controlling the medical imaging device 1.

The control device 30 comprises the data processing unit 35, the decision support system 37, the computer-readable medium 32 and the processor system 36. The control device 30, in particular the data processing unit 35, is formed by a data processing system which comprises a computer.

The control device 30 comprises the image reconstruction device 34. A medical image dataset can be reconstructed via the image reconstruction device 34 on the basis of the acquisition data.

The medical imaging device 1 comprises an input device 38 and an output device 39, which are each connected to the control device 30. The input device 38 is embodied for inputting control information, e.g. image reconstruction parameters, examination parameters or similar. The output device 39 is embodied in particular for outputting control information, images and/or acoustic signals.

The solution according to an embodiment of the invention enables in particular a manual application of the findings-dependent rules, which would be necessary each time the protocol were used, to be dispensed with and an automated workflow to be implemented instead.

In this way it is possible to increase the reliability with which the findings-dependent rules are observed and applied. This enables an execution sequence of the examination to be realized in a simpler and more structured manner. In particular, the possibility to generate new examination jobs in the event of incidental findings can simplify the administration and accounting in cases of the kind. In particular where the management of a large fleet of radiological equipment is concerned, these dynamic rules may be managed centrally as a constituent part of the examination protocols and distributed to the individual devices. A separate maintenance and distribution of case-specific rules is thus rendered obsolete. An examination step may in particular comprise an acquisition and/or a reconstruction and/or an image processing operation.

By a machine learning algorithm, in the context of the present application, is understood in particular an algorithm that is embodied for machine learning. A machine learning algorithm may be realized for example with the aid of decision trees, mathematical functions and/or general programming languages. The machine learning algorithm may be embodied for example for supervised learning and/or for unsupervised learning. The machine learning algorithm may be embodied for example for deep learning and/or for reinforcement learning and/or for marginal space learning. In particular in the case of supervised learning, a functions class may be used which is based for example on decision trees, a random forest, a logistical regression, a support vector machine, an artificial neural network, a kernel method, Bayes classifiers or similar, or combinations thereof.

Possible implementations of the machine learning algorithm may use artificial intelligence, for example. One or more rule-based algorithms may be used alternatively or in addition to the first machine learning algorithm and/or to the second machine learning algorithm. Calculations, in particular when determining the classification system based on the set of training datasets and a machine learning algorithm, may be performed via a processor system, for example. The processor system may for example comprise one or more graphics processors.

In particular, data relating for example to a medical image, a protocol or a training dataset may be provided such that the data is loaded, e.g. from an area of a storage system, and/or generated, e.g. via a medical imaging device. In particular, one step or more steps or all steps of the method according to the invention may be performed automatically and/or via a component of a data processing unit, the component being formed by a processor system, for example. In particular, the medical imaging examination may be an examination via a medical imaging device and/or be performed via a medical imaging device.

The set of training datasets may in particular be provided by collecting a plurality of examination jobs together with the actual examinations. A decision support system can learn from this information, in particular recognize patterns. For example, it can be recognized in this way that most clinics also include a coronary reconstruction when a lung scan is performed. In this way it can quickly be identified that in the medical imaging examinations performed by a user, the user deviates compared to the majority of users performing similar medical imaging examinations.

By collecting, processing, analyzing and appropriately utilizing examination data of other clinics, the user is able to obtain information about the corresponding possibilities. To that end, according to the clinical indication, data revealing an optimal form of examination on the respective device would be collected and evaluated using the available technical facilities.

In particular, an examination recommendation with regard to an acquisition of imaging data can be generated via the decision support system, for example whether a spiral or a sequence is to be preferred or whether additional scans, in particular an additional late phase, might facilitate a better diagnosis. In particular, an examination recommendation with regard to a reconstruction of a medical image can be generated via the decision support system, for example whether a reconstruction using a different kernel would be better suited.

In particular, an examination recommendation with regard to an image processing operation can be generated via the decision support system, in particular which algorithms were to be preferred.

With the provision and analysis of the data of a number of experts, less experienced operators may also achieve optimal examination results through suitable use thereof with the aid of the decision support system. The capabilities of the available medical devices can be perfectly adapted to the indications and thus be exploited to the full. This is to the benefit of both inexperienced operators and experts, since less common examinations can also be performed in an optimal manner. Physicians in remote areas of the earth would also have the opportunity to share in the knowledge. This enables an improved examination to be performed for the patient. In modalities using radiation, the dose can also be significantly reduced in this way. The diagnosis can thus be made more quickly and accurately, in particular since the image material can be produced specifically for a given problem.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a list of examination steps, each examination step among the list of examination steps being assigned a respective instruction for adapting an examination protocol during a medical computed tomography imaging examination, the method comprising:
   generating the list of examination steps based on a set of training datasets and a machine learning algorithm, each training dataset among the set of training datasets including a respective training instruction and an examination parameter set, the examination parameter set relating to at least one of a training examination step assigned to the respective training instruction or an examination result assigned to the respective training instruction, each respective examination step among the list of examination steps being assigned the respective instruction, wherein at least one training dataset among the set of training datasets is generated based on a deviation from a selected examination protocol during a deviated examination step included in the selected examination protocol, the deviation including premature termination of the deviated examination step or skipping the deviated examination step.

2. The method of claim 1, further comprising:
generating the at least one training dataset by,
   recording the deviation as the respective training instruction of the at least one training dataset, the deviation being initiated manually by a user, and
   recording the examination parameter set of the at least one training dataset as relating to at least one of the deviated examination step or to the examination result of the deviated examination step.

3. A non-transitory computer-readable medium including stored program sections, readable and executable by a data processing system to perform the method of claim 1 when the program sections are executed by the data processing system.

4. A method for training a decision support system for an examination via a medical imaging device, the method comprising:
   training the decision support system based on a set of training datasets and a machine learning algorithm such that the trained decision support system is configured to generate an examination recommendation for the examination via the medical imaging device based on an examination job, each respective training dataset among the set of training datasets including a respective training examination job and respective examination information, the respective examination information relating to a medical computed tomography imaging examination performed based on the respective training examination job,
   wherein at least one training dataset among the set of training datasets is generated based on a deviation from a selected examination protocol during a deviated examination step included in the selected examination protocol, the deviation including premature termination of the deviated examination step or skipping the deviated examination step.

5. The method of claim 4, wherein
the respective training examination job includes a training instruction,
the respective examination information includes an examination parameter set, the examination parameter set relating to at least one of a training examination step assigned to the training instruction or an examination result assigned to the training instruction,
the examination recommendation includes a list of examination steps generated based on the set of training datasets and the machine learning algorithm, each examination step among the list of examination steps being assigned a respective instruction for adapting an examination protocol during a medical imaging examination.

6. The method of claim 5, wherein the respective training examination job includes an image generation job performed during the medical computer tomography imaging examination, and the respective examination information includes at least one of acquisition parameters of the image generation job or reconstruction parameters of the image generation job.

7. The method of claim 4, wherein the respective training examination job includes an image generation job performed during the medical computed tomography imaging examination, and the respective examination information includes at least one of acquisition parameters of the image generation job or reconstruction parameters of the image generation job.

8. The method of claim 4, wherein
the respective training examination job includes an image processing job; and
the respective examination information includes image processing parameters by which the image processing job was performed during the medical computed tomography imaging examination.

9. A decision support system; trained based on the method of claim 4.

10. A medical imaging device comprising the decision support system of claim 9.

* * * * *